US006960202B2

(12) United States Patent
Cluzeau et al.

(10) Patent No.: US 6,960,202 B2
(45) Date of Patent: Nov. 1, 2005

(54) HAND-HELD APPARATUS FOR SPRAY CRYOTHERAPY

(75) Inventors: Christian Cluzeau, Salins les Bains (FR); Jacky Desbrosse, Huiron (FR)

(73) Assignees: Cryonic Medical, Salins les Bains (FR); Vallourec Composants Automobiles Vitry, Vitry le Francois (FR)

( * ) Notice: Subject to any disclaimer, the term of this patent is extended or adjusted under 35 U.S.C. 154(b) by 63 days.

(21) Appl. No.: 10/398,733

(22) PCT Filed: Oct. 15, 2001

(86) PCT No.: PCT/FR01/03190

§ 371 (c)(1),
(2), (4) Date: Apr. 9, 2003

(87) PCT Pub. No.: WO02/30309

PCT Pub. Date: Apr. 18, 2002

(65) Prior Publication Data

US 2004/0102768 A1 May 27, 2004

(30) Foreign Application Priority Data

Oct. 13, 2000 (FR) .............................................. 0013128

(51) Int. Cl.[7] .............................................. A61B 18/18
(52) U.S. Cl. .......................................... 606/26; 606/20
(58) Field of Search ........................ 606/20–26; 607/96, 607/104, 107, 108–112, 114; 600/131

(56) References Cited

U.S. PATENT DOCUMENTS

| 5,901,723 A | * | 5/1999 | Ames .......................... 135/66 |
| 5,916,212 A | * | 6/1999 | Baust et al. .................. 606/22 |
| 6,141,985 A | * | 11/2000 | Cluzeau et al. ............... 62/293 |
| 2001/0018551 A1 | * | 8/2001 | Komi .......................... 600/131 |

FOREIGN PATENT DOCUMENTS

| DE | 195 48 652 | 10/1997 |
| FR | 2 775 589 | 9/1999 |

* cited by examiner

*Primary Examiner*—Michael Peffley
(74) *Attorney, Agent, or Firm*—Young & Thompson (57) ABSTRACT

A self-contained cryotherapy apparatus adapted to be operated with one hand, using flashing temperature of a cartridge liquefied gas ($CO_2$) sprayed in partly solid phase onto the epidermis. The cartridge support and the ejection and expansion system are aligned therewith and in the axis thereof, inside a housing whereof the median part acts as handle to be grasped by the adult user's hand, whereof the upper part includes an input for inserting the cartridge with its head down and into the housing axis and striking it or for removing it after use, and whereof the lower part includes a calibrated opening forming a passage for the sprayed gas substantially in the housing axis and elements for controlling its effect on the epidermis.

12 Claims, 5 Drawing Sheets fig.1 fig.2 fig.3 fig. 6　　　　fig. 7

HAND-HELD APPARATUS FOR SPRAY CRYOTHERAPY

The invention relates to a self-contained spray cryotherapy apparatus adapted to be manipulated with one hand, particularly efficient in the treatment of pain, inflammations, or for stimulating the circulation: it is well known that cold brings about a vasomotor reflex and an intensification of the action of draining, and even procures a muscular relaxation by lowering the muscular tonus: it is well known that cold makes it possible to obtain a reflex response.

In this respect, it is recalled that cold is much more efficient than heat, provided, however, that the treatment is effected with an intense cold which must, in addition, provoke a drop in temperature of the zone to be treated in order to take the epidermis from its normal temperature (about 32° C.) to a temperature included between 2° C. and 5° C. where the action of cold is maximum on the cutaneous receptors. Accessorily, it has been observed that the efficiency of the thermal action of the gas sprayed in liquid phase is further increased in large proportions by the complementary action of the pressure that the flux exerts on the epidermis. The majority of cryotherapy apparatus use as source of cold either refrigerated air, or more generally liquid nitrogen whose use remains subject to numerous constraints most often limiting the mobility of the treatment apparatus; in the domain of sport, where cryotherapy finds one of its major applications, use is currently made of small aerosols of gas under low pressure whose expansion around a local traumatism produces cold not exceeding −25° C. with insufficient drop in temperature and speed of cooling.

On the other hand, European Patent EP-0.633.008 in the name of the Applicants has already proposed using as source of cold for the cryotherapy, compressed carbonic anhydride ($CO_2$) of which an intrinsic characteristic is to procure a flashing temperature of −78° C. at atmospheric pressure. According to the teachings of this Patent, the use of carbonic anhydride in the form of a liquid/vapour mixture makes it possible to maintain a constant pressure in the recipient during its emptying; this pressure which is none other than the saturating vapour pressure, depends directly on the temperature of the recipient. Thus, by expanding to atmospheric pressure, the carbonic anhydride is in two phases: solid and gaseous. It is the solid phase, also called dry ice, which makes it possible to draw off the maximum of calories at the level of the epidermis of the patient to be treated. In effect, upon its contact, the solid carbon dioxide, or dry ice, sublimates, thus evacuating a large quantity of heat. It is therefore essential to draw from the recipient the liquid phase of the carbonic anhydride in order to obtain both an intense cold and a temperature drop which is as rapid as possible.

Patent FR-2.775.589 in the name of the Applicants has already proposed a self-contained, light and portable apparatus capable of producing an intense cold procuring a very rapid temperature drop, and this under maximum conditions of thermal safety using by way of principal the flashing temperature (of the order of −78° C. at atmospheric pressure) of the carbonic anhydride ($CO_2$) or equivalent in liquid/solid phase; to that end, the apparatus comprises a reservoir of liquefied $CO_2$ under pressure of which the head is connected to a system of ejection and of expansion of the liquid/solid $CO_2$, and comprises members for controlling the ejection system and for monitoring the temperature of the zone of use; this apparatus is noteworthy in that the head of the $CO_2$ reservoir is arranged on the apparatus so that, during the whole period of use, only the liquid part of the $CO_2$ inside the reservoir comes into contact with said head in order to be drawn off and propelled towards the zone of use.

This apparatus has been designed to be used by professionals, with the drawback that it cannot be used by the individual in a domestic context. The present invention therefore relates to an apparatus improved in order to be used by any adult user simply and without the least danger occurring in the event of use under poor conditions.

In this respect, there is proposed, according to the invention, a self-contained cryotherapy apparatus adapted to be manipulated with one hand, using the expansion temperature and pressure of a liquefied gas sprayed in at least partially solid phase on a human or animal epidermis, such as $CO_2$ or equivalent, contained under pressure in a removable cartridge, of which the drawing off head, which is connected by a support to a controlled system of ejection and of expansion of the liquefied gas, is such that, for the whole duration of a projection, only the liquid part of the gas inside the cartridge comes into contact with said drawing off head and this apparatus is noteworthy in that the support of the cartridge and the controlled ejection and expansion system are disposed substantially in line and in the axis of the apparatus, inside an ergonomic housing whose axis corresponds to that of the apparatus, of which the median part serves as handle to be grasped by the adult user's hand and comprises a member for controlling the controlled gas ejection and expansion system of which the upper part presents an inlet for introducing into its support the cartridge, head down and in the axis of the housing, and for striking it or for withdrawing it after use, and of which the lower part comprises a calibrated opening forming a passage for the sprayed gas substantially in the axis of the housing and means for holding the outlet nozzle of the controlled ejection and expansion system at the required distance with respect to the zone of the epidermis to be treated.

It is therefore question of a light, compact apparatus able to operate under the conditions of intense cold as recalled in the preamble, only when it is grasped in the hand and arranged opposite the zone to be treated in virtually vertical position in order to obtain a projection of gas in liquid phase. In this respect, any other inclined position would lead to spraying the gas in gaseous phase, i.e. at a temperature without danger for the user.

According to several secondary characteristics which will be detailed hereinbelow, the apparatus according to the invention further comprises a certain number of devices guaranteeing the maximum safety of use; in particular, it is question of the particular shape of the apparatus which fits perfectly in the palm of a clenched hand, procuring an obligatory position for controlling the projection of the cryogenic line thanks to a double electrical control actuated by two different fingers of the hand maintaining the apparatus in vertical position; it is also for purposes of safety of use that, according to another important characteristic of the invention, there is provided a device for maintaining the nozzle ejecting the gas at the correct distance in order that it be absolutely impossible to cool the epidermis in the treatment zone below a temperature of 2° C., in any case before the cartridge of gas equipping the apparatus is totally empty. Finally, and according to a last characteristic, it is provided to complete the preceding protection systems by temperature sensors procuring within a desired time an alarm for the user and/or interrupting the projection in the hypothesis of the epidermis being in danger of necrosis, i.e. cooled to below 2° C.

Other characteristics and advantages will appear more readily from the description of a cryotherapy apparatus according to the invention for the general public, given hereinbelow by way of preferred, but in no way limiting example, with reference to the accompanying drawings, in which.

Referring to the Figures, the cryotherapy apparatus 1 which will be described by way of non-limiting example is particularly intended for so-called domestic use, i.e. by a user who is in principle not a professional.

Figure 1:
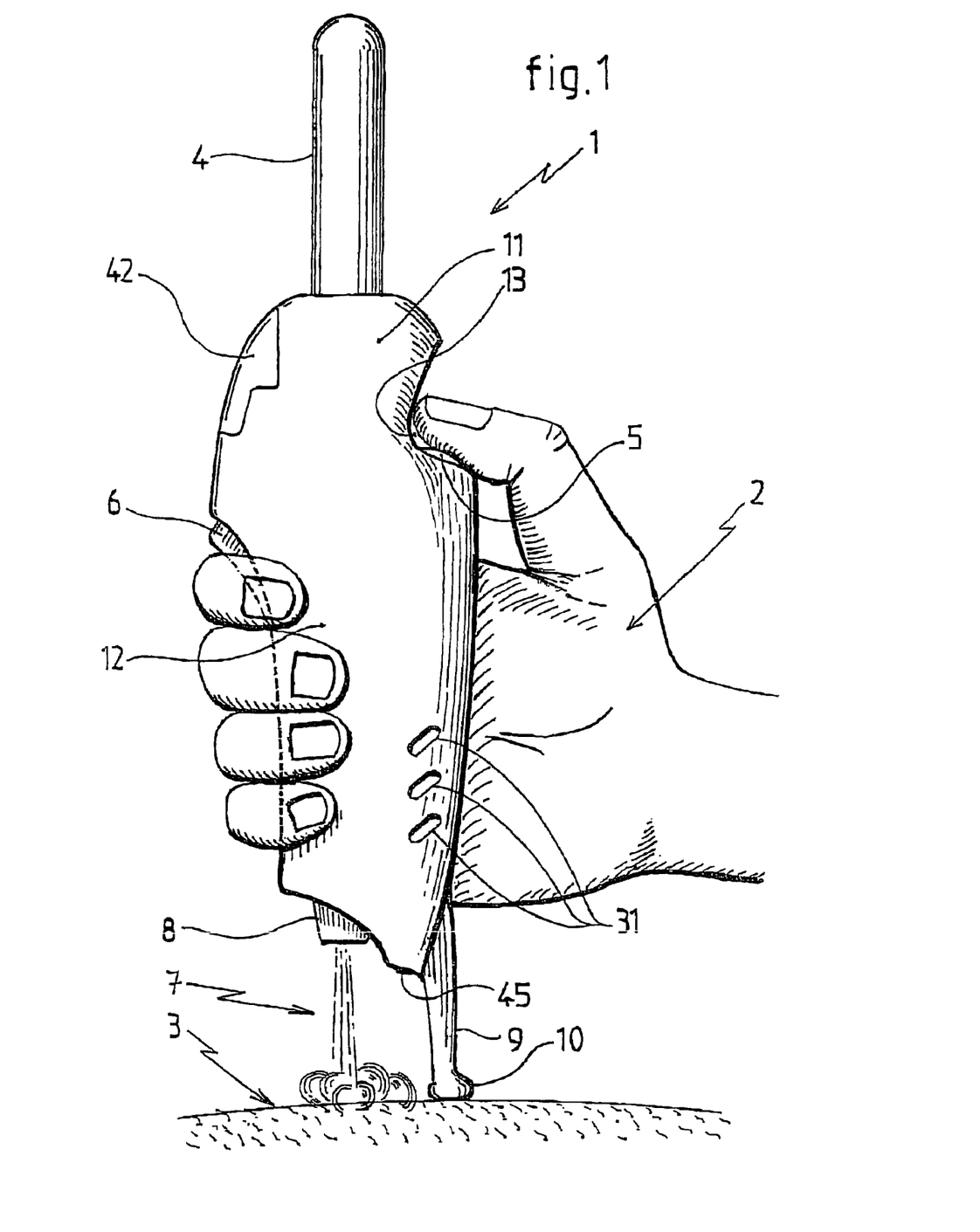
FIG. 1 shows a general view of the apparatus according to the invention maintained vertically in a user's right hand, at the correct distance from the epidermis to be treated.

In this respect, FIG. 1 shows a general view of the apparatus 1 grasped in a user's right hand 2 with a view to an application on the epidermis 3 of a region to be treated of a gas under pressure—preferably carbonic anhydride ($CO_2$)—, in at least partially solid phase coming from a disposable or re-usable cartridge 4, which is screwed, with its head down, in a cartridge support provided in the upper part of the apparatus 1 in order to maintain and strike an opening cap placing the contents of the cartridge 4 in contact with the cryogenic chain which will be described hereinbelow. For safety reasons, the projection of the gas on the epidermis 3 is controlled by the simultaneous action of a first switch 5 controlled by the thumb of the hand 2 and of a second switch 6 preferably having the form of a push-trigger 6 disposed in the region of the index finger of the hand 2 when the apparatus is grasped in the hand as represented in FIG. 1.

The $CO_2$ in liquid/solid phase 7 is ejected via a calibrated opening 8 which will be specified hereinbelow, located in the lower part of the apparatus and substantially in its vertical axis. For reasons of safety and in particular in order to avoid the temperature of the epidermis 3 under treatment passing below the critical temperature of 0° C. which creates a risk of necrosis of the epidermis, it is necessary to provide a minimum distance between the outlet 8 of the gas and the epidermis 3 to be treated. To that end, there is provided an excrescence in the form of a prop 9 which extends downwardly substantially in the axis of the apparatus 1 over a sufficient length to procure a suitable spacing between the outlet 8 and the epidermis 3, preventing a critical value of temperature, fixed for example at 2° C., from being attained when all the gas contained in the cartridge 4 is sprayed. It should be noted that the end of the prop 9 advantageously presents a shoe 10 making it possible to distribute the pressure of the apparatus over the patient's epidermis and to avoid injuring it during the treatment; in addition, the prop 9 is advantageously located on the proximal side of the apparatus, i.e. towards the user's arm, allowing him/her to better visualize the zone of treatment during the whole projection.

Figure 2:
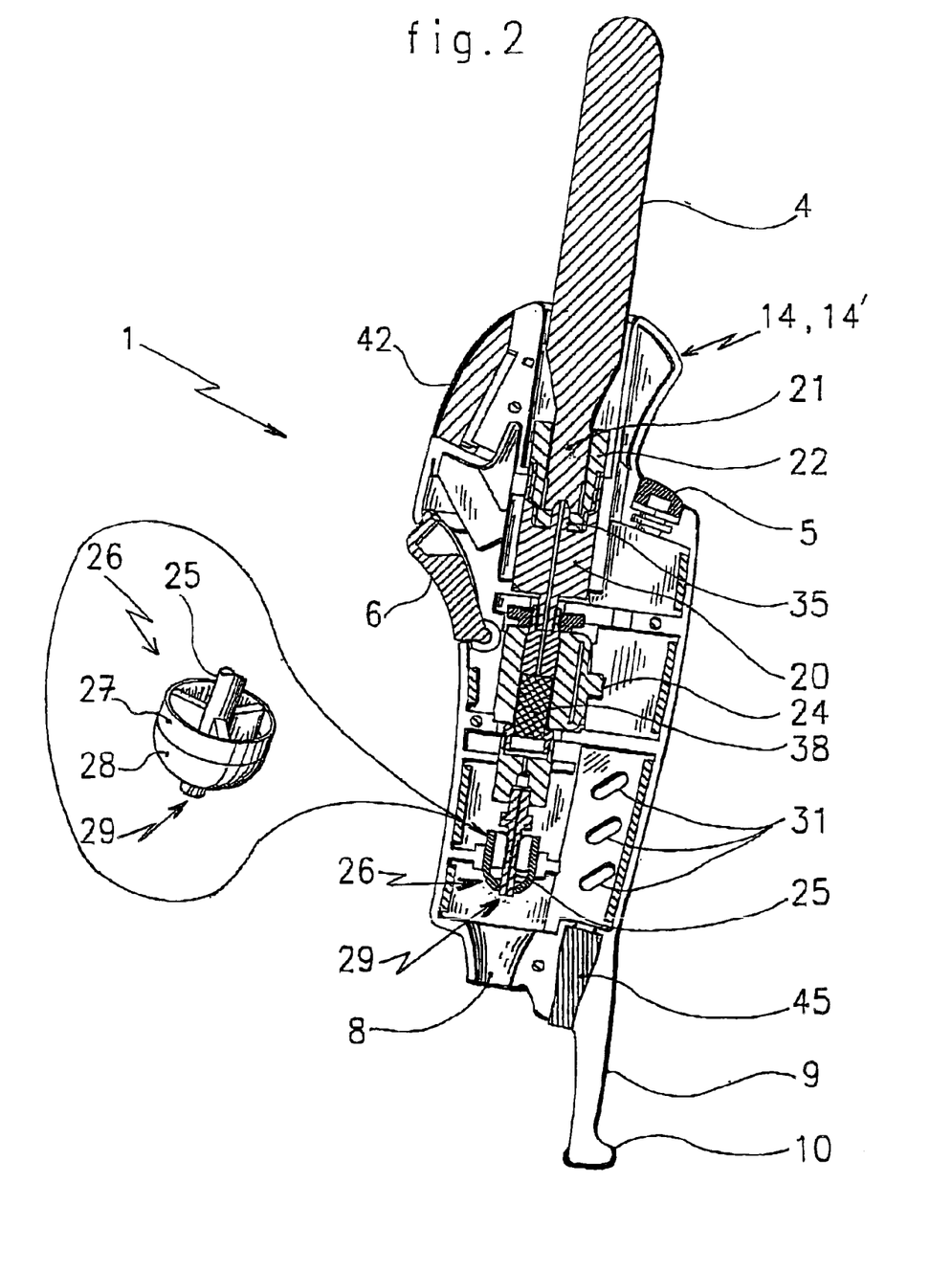
FIG. 2 shows in elevation and in median vertical section the apparatus along line II/II of FIG. 4, showing the internal structure of the members as well as their relative position in the apparatus.

In accordance with an essential configuration of the apparatus 1 according to the invention, the cryogenic chain shown in FIG. 2 is disposed substantially in line and in its axis, inside an ergonomic housing 11 of which the median part 12 (FIG. 1) serves as handle to be grasped by the adult user's hand; preferably, the median part 12 of the housing 11 is in fact substantially convex on the proximal side (i.e. towards the arm of the user), in order to follow the curvature of his thumb; in addition, a recess 13 in the upper part of this side of the housing 11 allows a movement of approach and of pivoting of the user's thumb to actuates control of the apparatus as will be stated hereinafter without interrupting the contact of the base of the thumb with the housing 11; on the distal side (i.e. the side most remote from the user), the median part of the housing is substantially concave in order to ensure complete grasp by the other four fingers, thus procuring a good grip of the apparatus 1 by one hand 2 of the adult user and to make it possible, by one or the other of his four fingers, to actuate at the same time the trigger 6 in order to control projection of gas 7.

Figure 4:
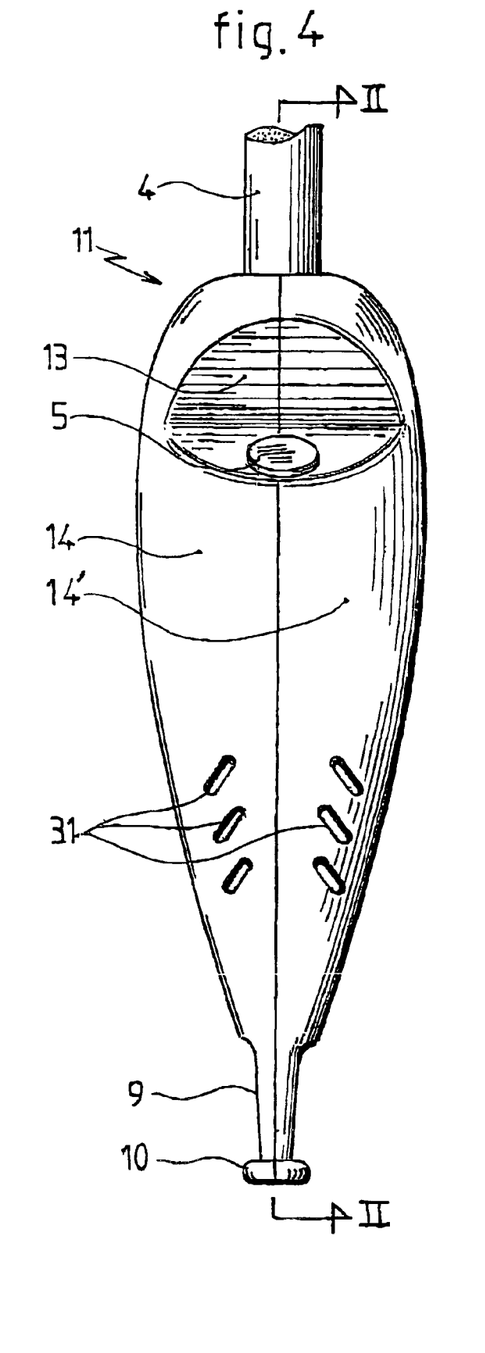
FIG. 4 is a front (proximal) view in elevation of the assembled apparatus.
Figure 5:
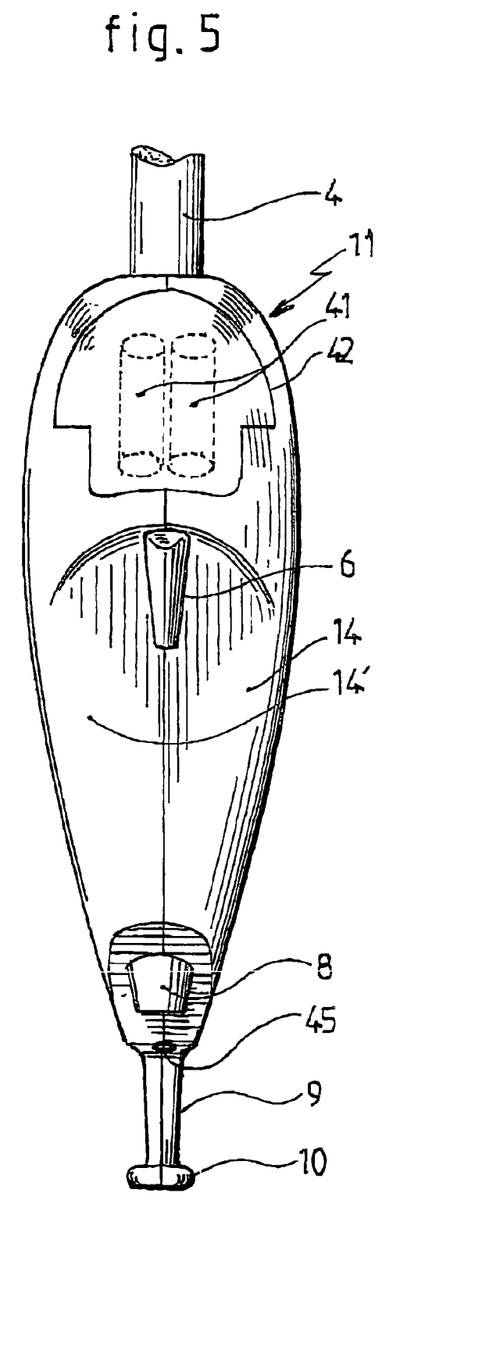
FIG. 5 is a rear (distal) view in elevation of the assembled apparatus.

According to a preferred embodiment of the apparatus 1, the housing 11 is preferably constituted by two half-shells 14, 14' of identical shape, assembled against one another in the median vertical plane of the housing 11. The general shape of each half-shell 14, 14' is represented in plan in FIG. 2, on the inner side of the housing 11; the outer shape of each half-shell 14, 14' is shown in front view in FIG. 1 and in side views in FIG. 4 for the proximal view and in FIG. 5 for the distal view.

According to an important arrangement of the apparatus in accordance with the invention, the median part 12 of the housing constituting the member for gripping the apparatus, has a mean section such that it fits perfectly in an adult's hand but that, reciprocally, it is difficult to hold in a child's hand; in this way, the latter will have difficulties in holding the apparatus in one hand, which, in addition to the electrical safety means which will be specified hereinbelow, constitutes a determining element for the safety of children.

Figure 3:
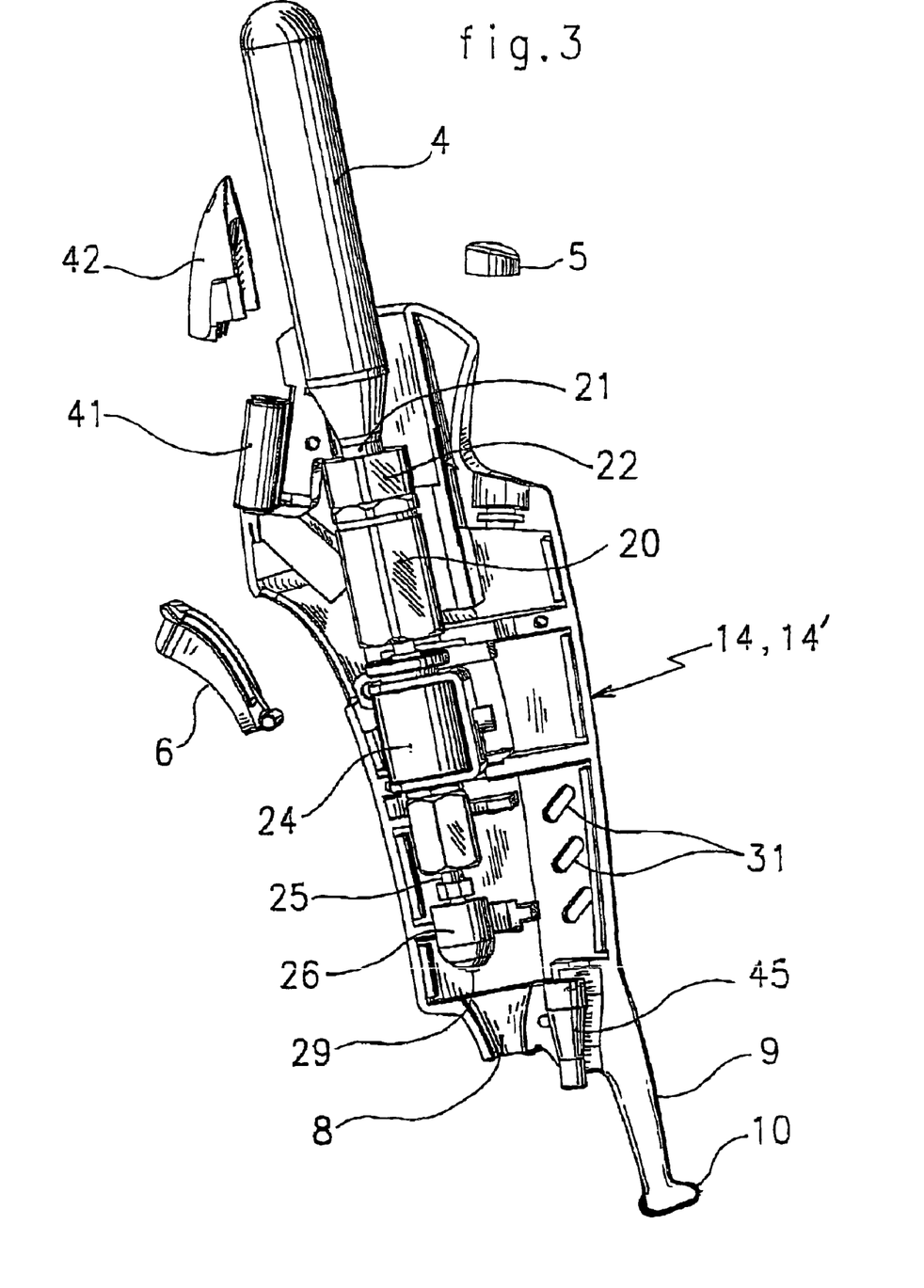
FIG. 3 is a view in elevation and in perspective of the apparatus of which one of the half-shells forming the envelope has been removed in order to show the internal members represented torn away but in relative position of functioning.

With reference to FIGS. 2 and 3, the cryogenic chain of the apparatus 1 will now be specified, disposed substantially in line in the axis of said apparatus, and maintained in correct position thanks to housings provided inside the half-shells 14 and 14' in which each of the elements constituting the chain fits precisely with the result that, after the two half-shells 14, 14' are assembled, the assembly is totally rigid.

The cryogenic chain successively comprises, in the upper part of the apparatus 1, a support 20 receiving, on the upper side, the drawing off head 21 of the cartridge 4 via a nut 22 forming connecting piece and, on the other side, a nut 23 supporting a filter which will be specified hereinbelow, an in-line electrovalve 24 intended to place the gas in its liquid form coming from the cartridge 4 in communication with the gas ejection and expansion system constituted by a tube 25 of small inner diameter of the order of 0.5 mm. In accordance with an important characteristic of the apparatus 1 according to the invention, it is provided, for questions of safety already taken up in the preamble, to monitor the sprayed gas thermally; to that end, the tube 25 of the ejection and expansion system is associated with a cylindro-conical sleeve 26 shown in FIG. 2 torn away on a larger scale; the sleeve 26 is mounted coaxially thanks to a radial wedging formed by at least three fins so that the cylindrical part 27 having an inner diameter greater than the tube 25, creates an air passage around said tube 25; the apex of the truncated part 28, extending the cylindrical part 27 downwardly, comes flush with the end of the tube 25 forming the gas ejection nozzle 29, making an annular space 30 for the passage of air clearly smaller than in the cylindrical part 27 in order to create by VENTURI effect an aspiration of the ambient air through holes 31 made at the base of the housing 11 in order to limit in this way the temperature and the pressure in the region of the epidermis 3 to be treated.

According to another embodiment of the invention, it is also possible to monitor the outlet temperature and pressure of the gas ejection and expansion system by giving the calibrated opening 8 in the lower part of the housing 11 a general nozzle shape, for example in tulip form flaring in the direction of the nozzle 29 and disposed in the same axis, at a correct distance in order to mix the ambient air sucked through the holes 31 by VENTURI effect generated by the propulsion of the gas.

It goes without saying that the two thermal regulation systems which have just been described may be combined in order to adjust the temperature and pressure of the sprayed gas 7 even more finely.

The members constituting the cryogenic chain inside the apparatus will now be described in detail, and this with reference to FIGS. 2, 6 and 7.

The cartridge 4 of CO2, medicalized as the case may be, and liquefied under a pressure of about 50 bars is in fact a cartridge conventionally comprising a metal recipient of cylindrical shape, closed at one end, quite similar to but smaller than the cartridges used in prior Patent FR 2 775 589 already cited; at the other end, the cartridge is provided with a drawing off head 21 arranged to cooperate with a support for use 20. The drawing off head 21 is constituted by an externally threaded cylindrical connector, a cap 401 which is intended to close the cartridge before it is placed in position in the apparatus, and an internally and externally threaded nut 22, the internal thread of the nut 22 being screwed on the thread of the connector of the drawing off head 21 in order to maintain the cap 401 in place. The cartridge 4 is in principle disposable taking into account its particular use, but might also be refilled if necessary; the cartridges contain CO2 in a quantity sufficient for a treatment of about 15 seconds. The drawing off system comprises, as in the prior art, a system for automatic percussion of the cartridge, ensuring the necessary tightness during and after the perforation of the cap 401 for example made of bronze, obturating the cartridge 4. Similarly, the screw pitch of the nut 22 which is screwed above the drawing off head 21 of the cartridge 4 has been voluntarily chosen from little used pitches so that it is not possible to use cartridges which are not in conformity.

Figure 6:
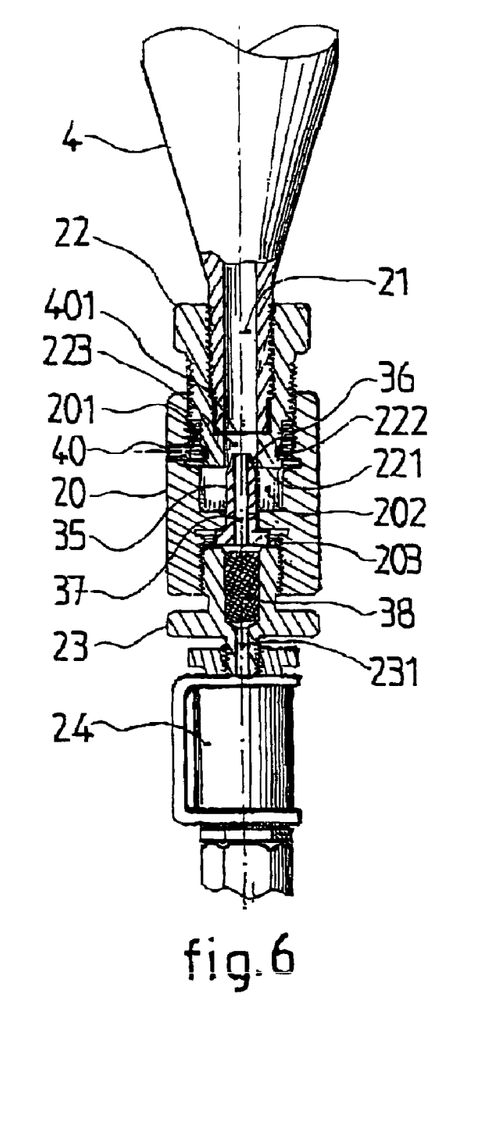
FIG. 6 is a partial representation on a larger scale of the cryogenic chain showing in detail the drawing off head of a gas cartridge mounted on its support inside the apparatus, just before the percussion of its closure cap.
Figure 7:
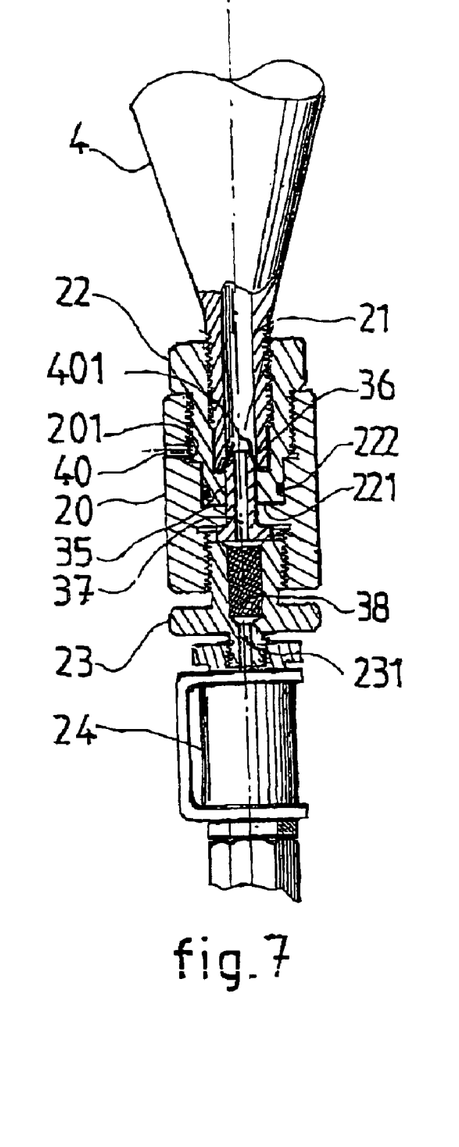
FIG. 7 is the same as the preceding Figure, except that the cartridge is shown totally engaged on its support after percussion of its cap.

The system of percussion of the cartridges 4 is composed of three parts in accordance with FIGS. 6 and 7. A cylindrical support 20 comprising on the cartridge side a first internally threaded inlet chamber 201 in which is screwed the nut 22 previously mounted on the drawing off head 21 obturated by the bronze cap 401; in the axis of this first chamber 201 and opening thereinto, a second chamber 202, of smaller diameter, collaborates with the end 221 of the nut 22 of diameter smaller than the threaded part of said nut in order to ensure total tightness, thanks to an outer O-ring 222 mounted in the area around said end 221, between the cartridge 4 and the rest of the device, as soon as the striker 35 perforates the cap 401. The striker 35 forming the second part of the system is constituted by a point 36 and is fast with the support 20 which may engage in the hollow end part 223 of the nut 22 surrounding the drawing off head 21 until it comes into contact with the cap 401 when the engagement of said nut 22 in the support 20 is sufficient to ensure connection of the assembly; at that instant, the point 36 is in contact with the cap 401 and the O-ring 222 is in contact with the walls of the chamber 202 ensuring its tightness with the drawing off head 21; it then suffices, as shown in FIG. 7, to continue to screw the cartridge 4/nut 22 assembly inside the support 20 in order to perforate the cap 401; the CO2 can then expand towards the downstream part of the support 20, passing firstly through a longitudinal channel 37 provided to that end in the axis of the striker 35 which opens out in a third coaxial chamber 203 of the support 20 necessary for positioning the percussion system and supporting in the flow of the liquid CO2 a filter 38 intended to retain possible residues contained in the cartridge 4. The filter 38 is capped by a nut 23 cooperating with an internal thread of the chamber 203 in conventional manner. The nut 23 is axially traversed by a channel 231 and it is provided on its downstream face with a threaded axis making it possible subsequently to implant the input of the electrovalve 24.

The latter, chosen from high-pressure electrovalves, allows the opening and closure of an axial channel extending the preceding channel 231 by simple control of an electromagnet disposed in the axis of the electrovalve. At the output of the electrovalve 24, is mounted the expansion tube 25 extending, if necessary, in the cylindrico-conical sleeve 27 thermally monitoring the flux of CO2. It will also be noted that, up to the outlet of the electrovalve 24, the CO2 is always in its liquid form and there is therefore no formation of solid carbon dioxide capable of preventing the circulation of the fluid; for the purpose of regulating the outlet flowrate of the liquid CO2, the expansion tube 25 is given a very small internal diameter, of the order of 0.5 mm; in order to avoid the formation of a plug of ice at the outlet of the expansion tube, a tube made of PTFE is preferably used and, taking into account the pressure of the CO2 of the order of 50 bars at the outlet of the cartridge 4, the speed of flow of the CO2 inside the tube 25 is sufficiently high to evacuate to the outside the solid carbon dioxide in micronized particles.

When the cartridge 4 has delivered all its contents in liquid phase, it is necessary to proceed with its replacement or, in accordance with another embodiment, with its refill. To that end, the cartridge 4 should be withdrawn from its support 20 and the problem is then raised of previously evacuating the residual gas inside the cartridge before it is completely withdrawn, in order to avoid a sudden recoil which may, in addition, be accompanied by a detonation. In order to bleed the cartridge before its withdrawal, there is therefore provided a bleed hole 40 connecting the outside of the chamber 202 disposed most upstream of the support 20, (i.e. the chamber not comprising the percussion member 35). This bleed hole 40 (FIG. 6) ensures the bleed of the residual gas at the moment of withdrawal of the cartridge 4 by unscrewing the nut 22 from its housing in the chamber 201 of the support 20; naturally, the internal geometry of this chamber 201 has been provided so that, as soon as the uncapped head of the cartridge 4 is disengaged from the percussion point 36, the residual gas is in contact with the bleed hole 40, i.e. with the outside, while the length of the thread of the nut 22 still engaged in the chamber 201 is still sufficient to maintain the assembly rigidly and to avoid any sudden recoil of the cartridge released from its support; it will therefore suffice, as soon as the hiss of the gas through the bleed hole 40 is heard, to wait for it to stop before continuing to unscrew the nut 22 and remove the cartridge 4, with a view to replacing it, without danger.

According to a particularly important characteristic concerning the safety of the apparatus, the electrovalve 24 supplied by batteries 41 advantageously disposed in a housing 42 (FIGS. 3 and 5) in the upper part of the distal face of the housing 11 (FIG. 5) and controlled, i.e. switched on, by the simultaneous pressing of the two switches 5 and 6 mounted in series in the electrical supply, i.e. between the batteries 41 and the coil of the electrovalve 24; as has already been stated, and in order to avoid any manipulation, particularly by children, the relative position of the two switches 5 and 6 projecting on the housing 11 is such that, when the median part of said housing is in an adult's hand, the first switch 5, preferably in the form of a push button, comes substantially under the user's thumb and the second switch 6, advantageously in the form of a trigger, can be actuated by at least one of the other four fingers of the hand. It has been seen that the two switches 5 and 6 were, to that end, located respectively on either side of the housing 11, diametrally opposite in its median plane.

According to a final characteristic of the invention, the apparatus 1 which has just been described may advantageously be completed by a complementary member for monitoring the temperature of the zone of use in order to avoid the drop in temperature favourable for the treatment causing necroses of the tissues; to that end, and according to a particular embodiment of the invention, it is provided to add a temperature threshold detector 45 coupled to control electronics and capable of functioning remotely without contact with the zone of use or of care, in accordance with FIGS. 2 and 3. Placed in the lower part of the housing 11 for the optics of the detector 45 to be centred in the direction of the zone to be treated, the preferred temperature threshold detector has been chosen as an infra-red pyrometer preferably operating with a D.C. supply of 12 volts like the electrovalve 24; in practice, the focal distance of the optics of the pyrometer 45 is chosen so that the field of vision corresponds as completely as possible to the target to be measured on the epidermis in order to obtain a correct and precise temperature reading. To that end, the position of the pyrometer 45 is calculated precisely in order that its distance to the zone of treatment not be either too short, as in that case the heat gradient of the skin becomes so great that the temperature of the treated zone and the temperature of the zone scrutinized by the pyrometer are very far from each other, with the consequence of rendering the alarm order random, nor be too far, which would almost surely lead to a superposition between the jet of solid carbon dioxide and the infra-red radiation, with the consequence that the pyrometer would read the temperature of the jet more surely than that of the zone to be supervised.

According to an accessory characteristic, the threshold detector of the pyrometer 45 is regulated to a temperature of the order of 5° C. in order to conserve a safety margin; according to a first embodiment, when the temperature threshold of the pyrometer 45 is attained, the control electronics which are associated therewith warn the user by a sound or visual signal and/or may cut off the supply of the electrovalve 24, suddenly stopping the projection of the $CO_2$; according to another embodiment, the pyrometer 45 can send a sound or visual signal when a first danger threshold is attained and cut off the electrovalve 24 when a second threshold is attained, for example around 2° C.

The apparatus 1 according to the invention, in accordance with one or the other of the embodiments which have just been described, may be used simply by any adult, non-professional user. To that end, it will suffice for him to grip in his right hand, for example, the median part 12 of the housing 11 of the apparatus, to introduce in the upper part thereof a new cartridge 4 and screw it in its support 20 until percussion of its cap 401 is obtained; the apparatus is then ready to operate and it will suffice for the adult user to bring it towards the epidermis 3 on which it is desired to effect a cryotherapy, maintaining it vertically until the end 10 of the prop 9 is in contact with the zone to be treated; at that moment, and the apparatus being maintained vertically, it will suffice for the user to press simultaneously on the button 5 with his thumb and on the trigger 6 with his index finger in order to trigger off the electrovalve 24 and therefore the projection 7 of a flow of $CO_2$ in liquid/solid phase. In principle, the cartridge of the apparatus is provided for one operation, i.e. to take the zone to be treated from a temperature of about 32° C. to a temperature included between 2 and 5° C., and this in about 15 seconds. The thermal safety arrangements of the apparatus have already been seen hereinabove but it will nonetheless be observed that, when the apparatus is poorly positioned, voluntarily or not, i.e. when it is no longer in the vertical axis allowing the prop 9 to perform its role of separator fully, the diameter of the cartridge 4 is such that, very rapidly, the flow propelled via the nozzle 29 of the ejection and expansion system is in fact in gaseous form therefore without danger for the epidermis from the thermal point of view.

Finally, in accordance with a simpler embodiment of the apparatus according to the invention, it is possible to replace the electrovalve 24 and all its electrical controls by a purely mechanical device of the manually actuated mechanical valve type. This embodiment, not shown in the Figures, consists in replacing the electrovalve in the line of the cold by a transverse piston valve actuated by a lever arranged in the zone of grip of the body of the apparatus; in this way it suffices to tighten the trigger arranged within reach of the hand holding the apparatus in order to actuate the piston valve, which is, in fact, the same as placing in contact, upstream, the drawing off head of the cartridge 4 and, downstream, the liquefied gas expansion and ejection system.

In this simplified version of the apparatus, it goes without saying that the drawing off head of the cartridge may advantageously be obtained by a contraction of the end of the envelope of the cartridge provided with an adequate thread screwing directly in the cartridge support 20 comprising, as in the preceding variant, a percussion member 35; the cartridge thus simplified is obviously provided with a cap cooperating with said percussion member, as in the preceding variant.

In this embodiment, a detector of temperature of the zone to be treated is not necessarily provided, insofar as the quantity of gas contained in the cartridge in its simplified version is such that it is not possible to descend this side of the critical temperature even when the contents of this cartridge are totally ejected.

According to another arrangement which, moreover, is applicable to all the variants of the apparatus according to the invention, the prop 9 making it possible to arrange the nozzle 29 of the ejection system at the correct distance, may be replaced by a hollowed base of cylindrical, truncated cone or truncated pyramid shape, issing from the lower part of the housing 11 and extending downwardly substantially in the axis of said housing over a determined length in order to ensure a sufficient safety distance as explained hereinabove concerning the prop 9. This hollow base device presents, furthermore, the advantage of a better stability of the apparatus at rest and it naturally avoids any error of positioning of the apparatus above the zone of the epidermis to be treated.

Functioning of the apparatus in its simplified mechanical version is extremely simple, which renders it particularly suitable for general public use.

What is claimed is:

1. In a self-contained cryotherapy apparatus adapted to be manipulated with one hand, to spray on a human or animal epidermis (3) a gas contained under pressure in a removable cartridge (4), the apparatus having a drawing off head (21), which is connected by a support (20) to a controlled system of ejection and expansion of the gas, the support (20) of the cartridge and the controlled ejection and expansion system being disposed substantially in line along the axis of the apparatus, there being an ergonomic housing (11) surrounding the apparatus whose axis corresponds to that of the apparatus, and of which a median part serves as a handle to be grasped by an adult user's hand (2), the housing (11) having an inlet for introducing to said support said cartridge (4) head down and along the axis of the housing (11) and for striking the cartridge and withdrawing it after use, a lower part of said housing comprising a calibrated opening (8) forming a passage for the sprayed gas substantially along the axis of the housing, and means (9) for holding an outlet nozzle (29) of the controlled ejection and expansion system at a required distance with respect to the zone of the epidermis to be treated; the improvement comprising an electrovalve (24) in line with the tube (25) for ejection of the gas, and two switches (5, 6) adapted to be actuated by the user's hand (2) and mounted in series in an electrical supply (41) of the electrovalve (24), the actuation of the electrovalve requiring the simultaneous pressing of the two switches (5, 6) by the user's hand (2) to actuate the electrical supply (41) of the electrovalve (24), the position of the two switches (5, 6) on the housing (11) being such that when the median part (12) of said housing is in an adult's hand (2), a first switch (5) comes under the user's thumb and the second switch (6) can be actuated by one or more of the other four fingers of the user's hand (2), said housing (11) being shaped to be substantially convex on a proximal side facing the user in order to follow the curvature of the user's thumb, a recess (13) in an upper portion of the housing (11) allowing the movement of approach of the thumb without interrupting the contact of the base of the thumb with the housing, the housing being substantially concave on a distal side away from the user for a complete grasp by a finger or fingers of the user.

2. Apparatus according to claim 1, characterized in that the tube (25) of the liquefied gas ejection and expansion system is a tube of an inner diameter of about 0.5 mm.

3. Apparatus according to claim 1, characterized in that the means for holding the nozzle (29) of the ejection system at the required distance from the epidermis (3) to be treated are constituted by an excrescence of a prop (9) issuing from the lower part of the housing (11) and extending downwardly, substantially parallel to the axis of said housing over a determined length in order to maintain the required distance, when the apparatus (1) is positioned opposite the epidermis (3).

4. Apparatus according to claim 1, characterized in that the cartridge (4) comprises a tubular body closed at one end and presenting at the other end a drawing off head (21) constituted by an externally threaded cylindrical connector, by a cap (401) which is intended to close the cartridge before it is placed in position in the apparatus.

5. Apparatus according to claim 4, characterized in that the drawing off head (21) of the cartridge is provided with an internally and externally threaded nut (22), the inner thread of the nut (22) being screwed on the thread of the connector of the drawing off head (21) in order to hold the cap (401) in place.

6. Apparatus according to claim 4, characterized in that the cartridge (4) is connected to the cartridge support (20) in the apparatus by screwing so as firstly to bring the cap (401) into contact with a fixed percussion member (35), extending in the axis of the support (10), then to pierce said cap (401) ensuring tightness of the assembly in order to draw off the gas in liquid phase via an axial channel (37) traversing right through the percussion device, connected downstream at its free end to the controlled expansion system, a bleed hole (40) between the inner space of the support (20) and the outside being provided radially in that part of said support (20) not comprising the percussion member (35) in order to bleed the residual gas in the empty cartridge during its unscrewing and before it is completely disconnected from the apparatus.

7. Apparatus according to claim 1, which further comprises means for monitoring the projected gas which consist in surrounding the outlet tube (25) of the ejection and expansion system by a cylindrico-conical sleeve (26) mounted coaxially thanks to a radial wedge of which the cylindrical part (27) has an inner diameter larger than a tube (25) in order to create a passage of air all around said tube and of which the apex of the truncated part (28) extending the cylindrical part (27) comes flush with the end of the tube (25) forming an ejection nozzle (29) arranging an annular space for the passage of air clearly smaller than in the cylindrical part (27) in order to create by VENTURI effect a suction of the ambient air through openings (31) made at the base of the housing (11) and thus to limit the temperature and pressure in the region to be treated.

8. Apparatus according to claim 1, which further comprises means for monitoring the projected gas constituted by the arrangement of the calibrated opening (8) in the lower part of the housing (11) having the general shape of a nozzle in the form of a tulip flared in the direction of the nozzle (29) of the tube (25) and is disposed in the same axis, at the correct distance from said nozzle and via openings (31) made at the base of the housing (11) so as to mix with the liquefied gas in the course of expansion of the ambient air sucked through openings (31) by VENTURI effect created by the propulsion of the gas.

9. Apparatus according to claim 1, which further comprises a means for thermally monitoring the epidermis (3) which is a detector (45) for detecting the temperature of the epidermis (3) acting without contact therewith.

10. Apparatus according to claim 9, characterized in that the detector is an infrared pyrometer (45).

11. Apparatus according to claim 10, characterized in that the focal distance of the infrared pyrometer (45) is such, on the one hand, that there is no interaction with the spraying of the liquefied gas, and, on the other hand, that the precise measurement of temperature is effected when the apparatus (1) is positioned at a suitable distance for the use envisaged.

12. Apparatus according to claim 10, characterized in that the infrared pyrometer (45) is coupled to a visual and/or sound alarm when the drop in temperature of the zone of use reaches a predetermined threshold, the pyrometer (45) in that case being able to automatically cut off the electrical supply of the electrovalve (24).

* * * * *